(12) United States Patent
Heaton et al.

(10) Patent No.: US 7,226,471 B2
(45) Date of Patent: Jun. 5, 2007

(54) PATIENT COOLING SYSTEM

(75) Inventors: Keith Patrick Heaton, Poole (GB); Mark Beard, Ferndown (GB); David Whyte, Wareham (GB); Peter Stacy, Ferndown (GB); Chris Coward, Wareham (GB)

(73) Assignee: KCI Licensing, Inc., San Antonio, TX (US)

( * ) Notice: Subject to any disclaimer, the term of this patent is extended or adjusted under 35 U.S.C. 154(b) by 23 days.

(21) Appl. No.: 10/785,547

(22) Filed: Feb. 24, 2004

(65) Prior Publication Data

US 2004/0186537 A1     Sep. 23, 2004

Related U.S. Application Data

(63) Continuation-in-part of application No. 10/290,938, filed on Nov. 8, 2002, now Pat. No. 6,945,987.

(51) Int. Cl.
    *A61F 7/00*     (2006.01)

(52) U.S. Cl. .................. 607/104; 607/108; 607/114; 5/421

(58) Field of Classification Search .......... 607/96, 607/104, 107, 108, 114; 5/421; 600/21, 600/22
See application file for complete search history.

(56) References Cited

U.S. PATENT DOCUMENTS

| | | | | |
|---|---|---|---|---|
| 2,104,589 A | * | 1/1938 | Hartman | 128/204.15 |
| 2,603,214 A | * | 7/1952 | Taylor | 128/204.15 |
| 3,283,520 A | | 11/1966 | Donohue et al. | |
| 3,710,791 A | * | 1/1973 | Deaton | 128/205.26 |
| 3,999,541 A | | 12/1976 | Tabor | |
| 4,000,749 A | * | 1/1977 | Busco | 600/21 |
| 4,170,998 A | | 10/1979 | Sauder | |
| 4,237,914 A | * | 12/1980 | Gantz | 52/2.19 |
| 4,506,511 A | | 3/1985 | Cameto et al. | |
| 4,572,188 A | | 2/1986 | Augustine et al. | |
| 4,638,519 A | | 1/1987 | Hess | |
| 4,660,388 A | | 4/1987 | Greene, Jr. | |
| 4,736,762 A | * | 4/1988 | Wayman | 52/2.14 |
| 5,044,364 A | | 9/1991 | Crowther | |
| 5,081,339 A | | 1/1992 | Stine | |
| 5,097,548 A | * | 3/1992 | Heck et al. | 5/482 |
| 5,331,991 A | * | 7/1994 | Nilsson | 135/93 |
| 5,350,417 A | | 9/1994 | Augustine | |
| 5,699,570 A | | 12/1997 | Wilkinson et al. | |

(Continued)

FOREIGN PATENT DOCUMENTS

EP     0164086     12/1985

(Continued)

*Primary Examiner*—Roy D. Gibson

(57) ABSTRACT

A patient cooling system comprises an inflatable patient mattress and a patient enclosure or tent supported by a framework of inflatable tubes drawing air off of the same air supply used to supply the mattress and to cool the tent. The framework of inflatable tubes is divided into left and right sections, which are further subdivided into lower body and upper body sections. An inflatable connector with a stem and protuberance is provided to secure the framework in a closed position. The patient-supporting mattress comprises a plurality of inflatable compartments extending transversely across the width of the mattress that can be alternately pressurized for pressure relief therapy. Radially collapsible, sleeved openings in the tent panel enable connection of conduits or patient care lines to the patient.

20 Claims, 11 Drawing Sheets

U.S. PATENT DOCUMENTS

| | | | |
|---|---|---|---|
| 5,749,109 A | 5/1998 | Kappel | |
| 5,817,147 A | 10/1998 | Wolf | |
| 5,832,919 A * | 11/1998 | Kano et al. | 128/205.26 |
| 5,928,273 A * | 7/1999 | Schmidt | 607/104 |
| 5,964,222 A * | 10/1999 | Kotliar | 128/205.26 |
| 6,210,427 B1 | 4/2001 | Augustine et al. | |
| 6,210,428 B1 | 4/2001 | Augustine et al. | |
| 6,245,096 B1 * | 6/2001 | Tomic-Edgar et al. | 607/107 |
| 6,282,737 B1 | 9/2001 | Vrzalik | |
| 6,730,115 B1 | 5/2004 | Heaton | |
| 2004/0050411 A1 * | 3/2004 | Lawrence | 135/128 |

FOREIGN PATENT DOCUMENTS

| | | |
|---|---|---|
| FR | 2754167 | 4/1998 |
| GB | 2 263 872 | 8/1993 |
| WO | WO 95/10211 | 4/1995 |
| WO | WO 97/42919 | 11/1997 |
| WO | WO 01/50988 | 7/2001 |

* cited by examiner

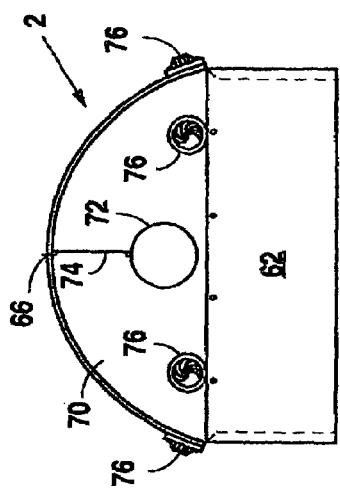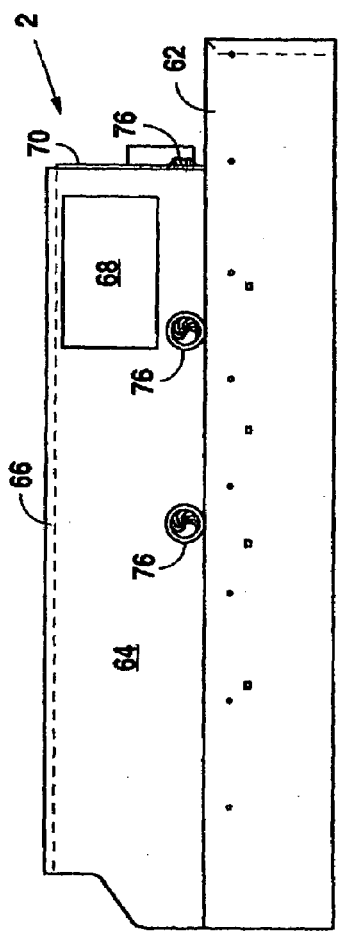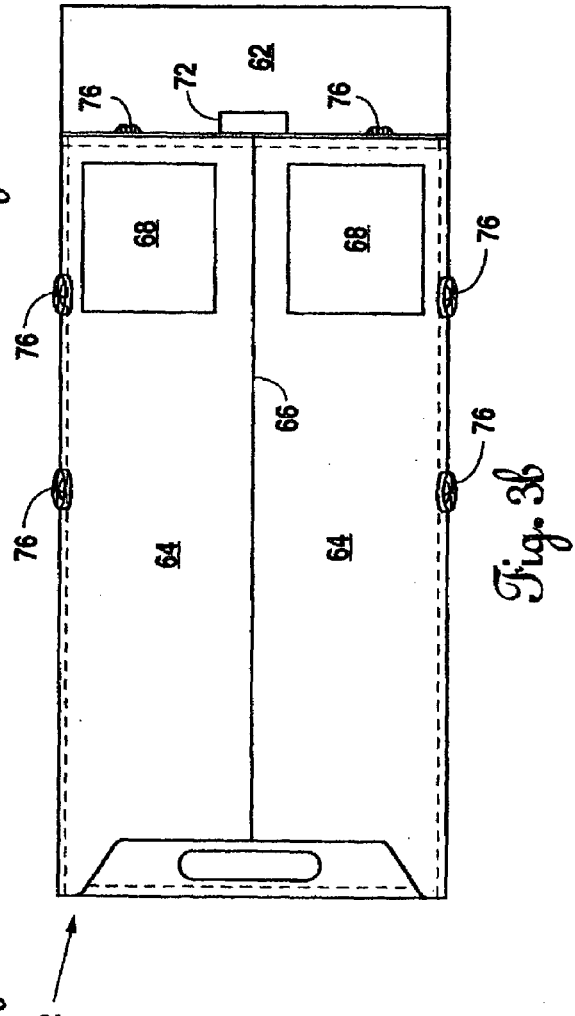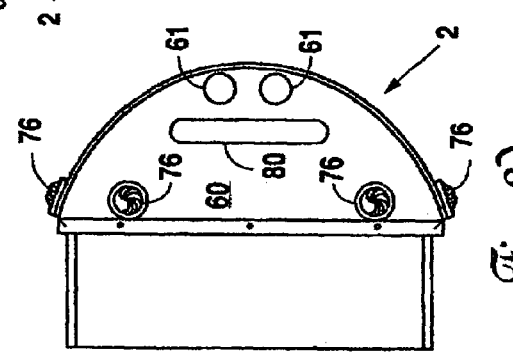

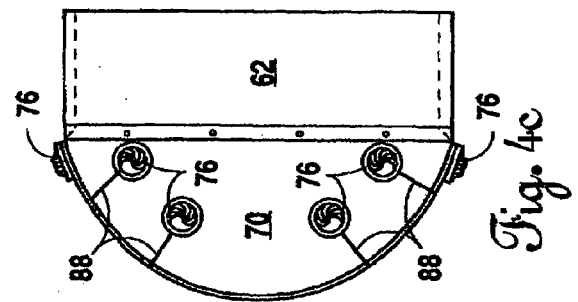
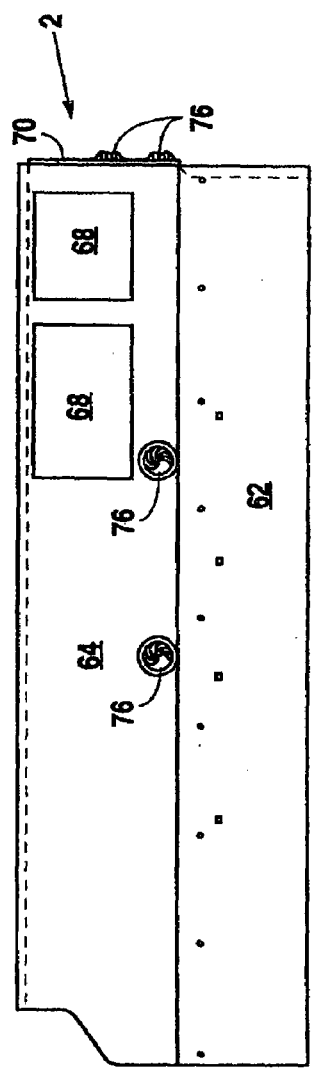
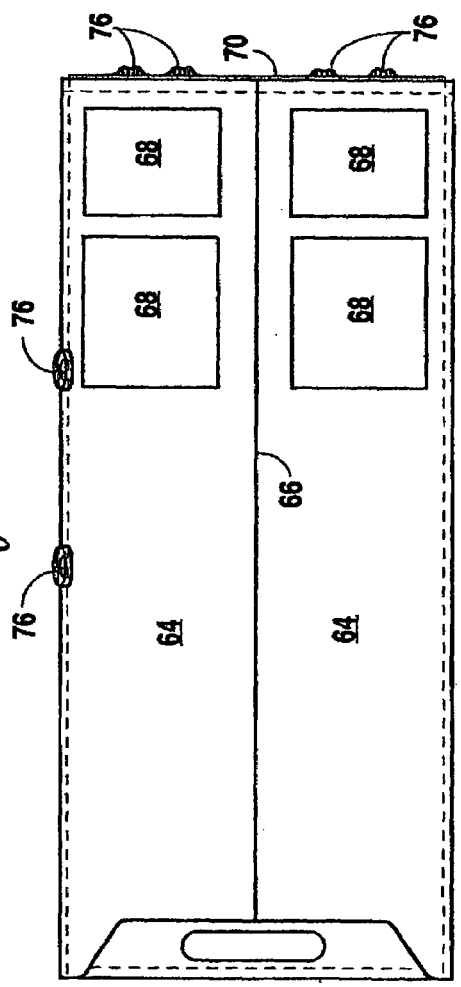

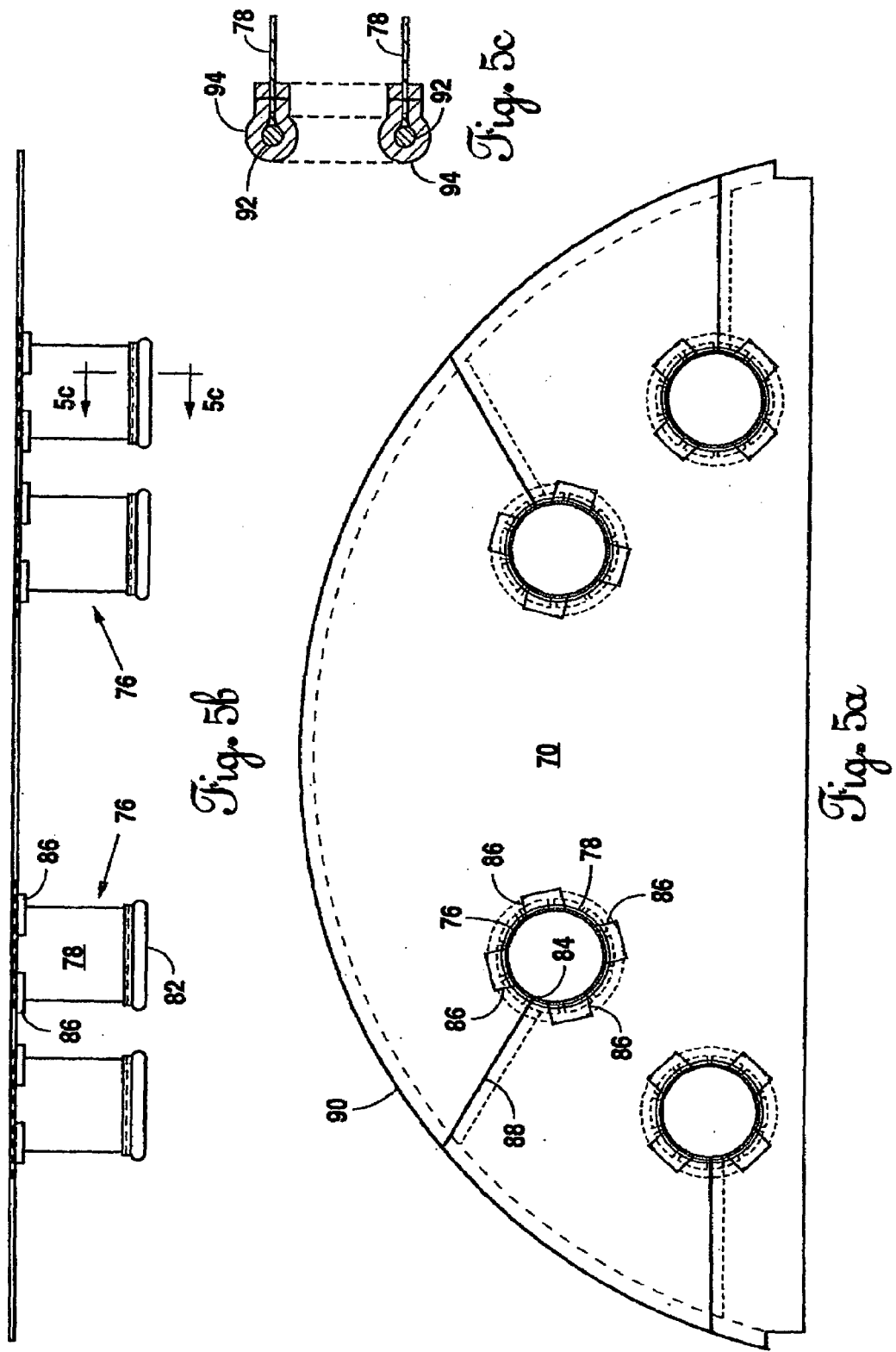

PATIENT COOLING SYSTEM

RELATED APPLICATIONS

This application claims priority to and is a continuation-in-part of U.S. patent application Ser. No. 10/290,938 filed Nov. 8, 2002, now U.S. Pat. No. 6,945,987 which is incorporated herein by reference.

FIELD OF THE INVENTION

This invention relates generally to systems for cooling a person for therapeutic purposes. More particularly, this invention relates to an enclosure or tent and support system for a patient who is to be cooled to a temperature below normal body temperature.

BACKGROUND

International patent applications published under WO 97/42919 and WO 00/27323, which are incorporated herein by reference for all purposes, describe systems for rapidly cooling a patient to a temperature a few degrees below normal blood temperature, e.g. in the range of about 32 to 34 degrees Celsius. This clinical procedure has been used with some success in reducing brain damage to cardiac or stroke patients.

SUMMARY OF THE INVENTION

The present invention provides an improved patient cooling system, which, according to a first feature of the invention, comprises an enclosure or tent having an inlet connected to an air cooling system, and an outlet which is connected to re-circulate exhaust air back to the inlet of the cooling system in order to minimize energy losses. Preferably, the enclosure is arranged so that it can be used on a variety of patient support devices including hospital bed frames, mattresses, and support devices mounted in an ambulance fitted with a suitable source of cold air.

Preferably, the enclosure is connected to a cooling system that includes an inlet for ambient air, a main blower that supplies air to the enclosure via the cooling section of a refrigeration system, and a re-circulation duct that connects an outlet from the air tent to the inlet side of the main blower.

Preferably the air inlet, main blower, and cooling section are all embodied in a single housing that is connected to the air tent through a dedicated hose set. Preferably the hose set is coaxial, and includes an inner tube for the inlet air to the enclosure surrounded by an outer tube for the return air. In this way, the outer air jacket advantageously isolates and insulates the colder inner tube from the ambient temperature.

Preferably, a valve is included in the return path to enable the proportion of re-circulated air to be varied, in accordance with operational requirements.

Preferably, the air tent is also provided with a separate outlet to the atmosphere, including a vane type valve to control the exhaust flow, which allows independent control of the pressure inside the enclosure. In this way it is possible to maintain the pressure within the preset limits even if the enclosure is subject to variable leakage.

Preferably, the patient is supported on a mattress system comprising a plurality of inflatable compartments, which can also be supplied with cooled air. Preferably, the compartments comprise elongate members that extend transversely across the width of the mattress, and can be alternately inflated to avoid any particular regions of the patient's body from being subjected to high pressure continuously.

According to a further feature of the invention, there is provided a patient support mattress comprising a plurality of transversely extending inflatable compartments, which are so arranged that each compartment can be alternately pressurized, either with relatively low pressure cold air, which assists in cooling the patient but provides relatively little support, or with higher pressure air which acts to support the patient, but provides relatively less cooling effect.

Preferably the mattress is connected into the re-circulating air supply system of the cooling enclosure, and may be provided with an additional blower to boost the pressure, for its high pressure supply.

According to a still further feature of the invention there is provided an air tent or enclosure for enclosing a patient in a controlled environment, comprising a plurality of panels of flexible material, and having an opening with releasable fastener means to enable a patient to be enclosed, at least one panel including an aperture or apertures to allow the passage of a duct or pipe to communicate with the interior of the enclosure, the aperture comprising a radially collapsible sleeved opening having a split along the side of the sleeve which communicates with a further split in the panel for introduction of the conduit, the sleeve being flexible and being adapted to be tightened around the conduit.

Preferably the outer edge of the sleeve is provided with a ring of hook or loop covered attachment material, which is adapted to cooperate with inter-engageable loop or hook material on the panel around the base of the sleeve, whereby the sleeve can be secured tightly around the conduit after it has been placed in position, by twisting the sleeve around the conduit and pressing the ring of material against the co-operating material on the panel.

Preferably the outer edge of the sleeve is also reinforced with a "split ring" of a resilient material such as aluminum. The split ring maintains the sleeve in a generally circular configuration as it is closed around the conduit and maintains the edge of the sleeve in continuous contact with the surface of the conduit.

The present invention encompasses several different embodiments of air tents. Some embodiments have tents that fully enclose the patient. Other embodiments have tents that allow the patient's head to protrude from the enclosure. In one embodiment, the air tent is supported by the internal air pressure of the tent. In another embodiment, the tent is supported by a framework of tent poles or equivalent structural support members. In yet another and currently preferred embodiment, the tent is supported by a framework of inflatable, collapsible tubes. In both the rod framework and the inflatable tube framework, the framework is preferably bifurcated along a line parallel to the longitudinal axis of the air tent, to enable the tent to be split open along the line of bifurcation. The framework is also preferably transversely split into two or more sections to enable the tent to flex with the articulation of a hospital frame.

These and other aspects and features of the present invention will be readily apparent to those skilled in the art from the following detailed description taken in conjunction with the annexed sheets of drawings, which illustrate the invention.

BRIEF DESCRIPTION OF THE DRAWINGS

FIG. 3a is a side elevation of one embodiment of a patient enclosure.

FIG. 3b is a plan view of the patient enclosure of FIG. 3a.

FIG. 3c is an end elevation of the enclosure of FIG. 3a.

FIG. 3d is an end elevation (opposite of FIG. 3c) of the enclosure of FIG. 3a.

FIG. 4a is a side elevation of another embodiment of a patient enclosure.

FIG. 4b is a plan view of the enclosure of FIG. 4a.

FIG. 4c is an end elevation of the enclosure of FIG. 4a.

FIG. 5a is an enlarged view of the end panel of FIG. 4c.

FIG. 5b is a plan view of the end panel of FIG. 5a.

FIG. 5c is a detailed view of a cross-section through part of the structure of FIG. 5a.

DETAILED DESCRIPTION

Based on the description and illustrations provided herein, the many benefits provided by the invented structure and methods of utilization are apparent. These described benefits, as well as those that are inherent to those skilled in the art, fall within the scope of the invention of the present patent application as limited only by the claims appended hereto.

Figure 1:
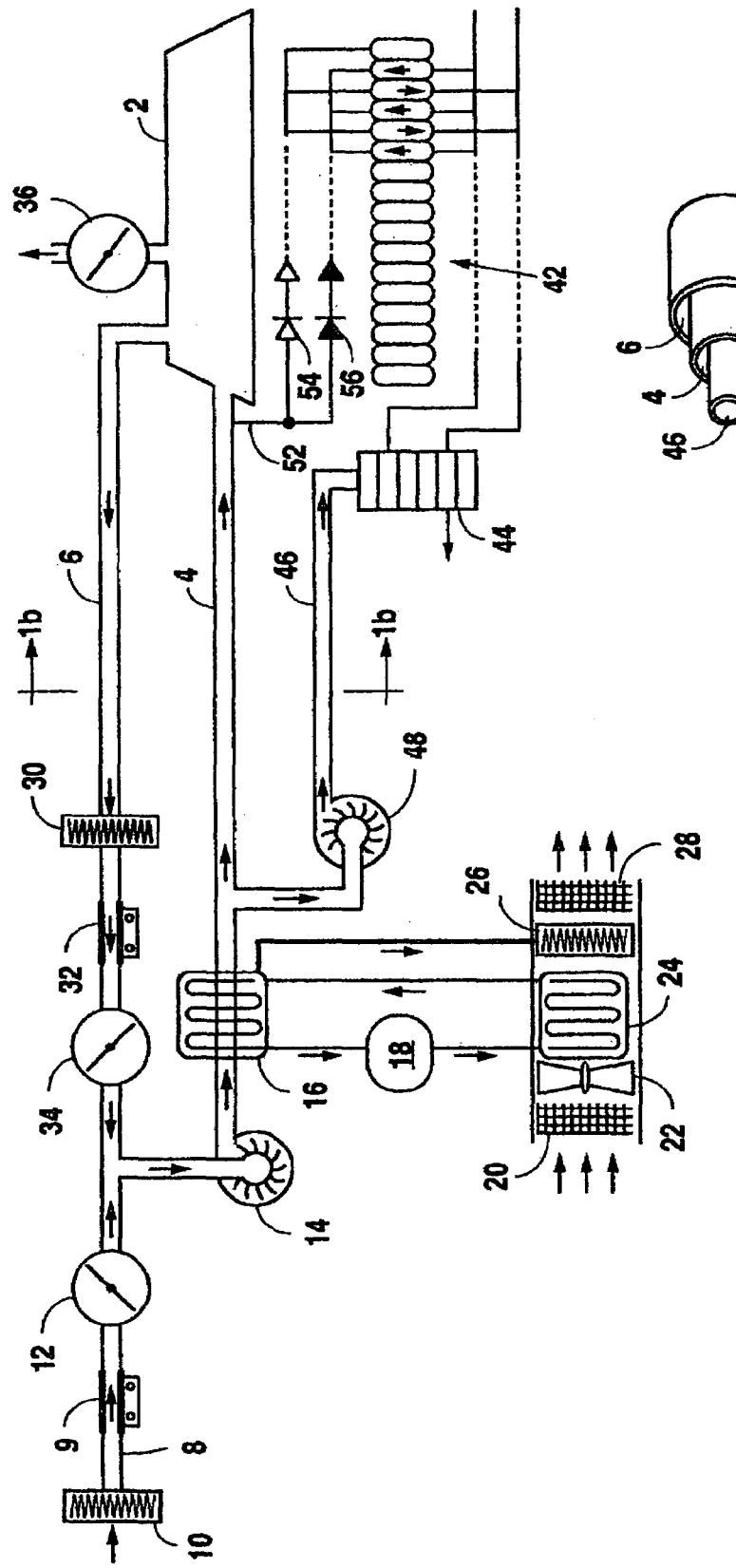
FIG. 1a is a schematic diagram of a patient cooling system according to the invention.
FIG. 1b is a partial cross-section view of the coaxial hose set according to the invention.

Referring to the drawings, FIG. 1a illustrates the general layout of a patient cooling system in accordance with the invention, comprising an air tent 2 forming an enclosure with a tent inlet duct 4 and a tent outlet duct 6. The air tent 2 is preferably constructed from panels of fabric material, as described in more detail below.

The air tent 2 is supplied with cool air through an air inlet duct 8, with a system intake filter 10, an intake flow sensor 9, and an intake valve 12 comprising a movable vane that communicates with a main blower 14. This pressurizes the air, and it then is passed through a heat exchanger 16, which comprises the evaporator section of a refrigeration circuit. The refrigeration circuit further comprises a compressor 18 and a condenser 24, which is provided in a conventional fashion with a condenser fan 22 having a condenser intake filter 20, a wick 26 for absorbing condensate drain from the evaporator section, and an outlet air filter 28.

Having passed through the heat exchanger 16 and thus being cooled, the air passes into the enclosure of the air tent 2 via the tent inlet duct 4, circulates past the patient, and leaves the enclosure via the tent outlet duct 6. The outlet duct 6 is connected by means of a re-circulation filter 30 to a re-circulation flow sensor 32 and a re-circulation valve 34 comprising a vane that can be moved in order to control the proportion of re-circulated air.

The air tent 2 is also provided with a vane type exhaust valve 36 that enables the pressure inside the air tent 2 to be independently controlled. In this way, the proportion of re-circulated air and the internal temperature of the air tent 2 can be controlled without unduly increasing or decreasing the total pressure inside the enclosure.

The apparatus also includes a patient-supporting mattress, indicated generally at 42 in FIG. 1a, which comprises a plurality of inflatable compartments or cells to which air is supplied through an arrangement of servo valves 44 which are connected to the cooling circuit by a conduit 46 containing a further blower 48. As illustrated in FIG. 1a and FIG. 1b, the conduit 46 is incorporated in a coaxial hose set, forming a central core thereof, so that the air passing through the conduit 46 is insulated from the ambient temperature by the outer coaxial passageways of the hose set that comprise tent inlet duct 4 and tent outlet duct 6.

Figure 2:
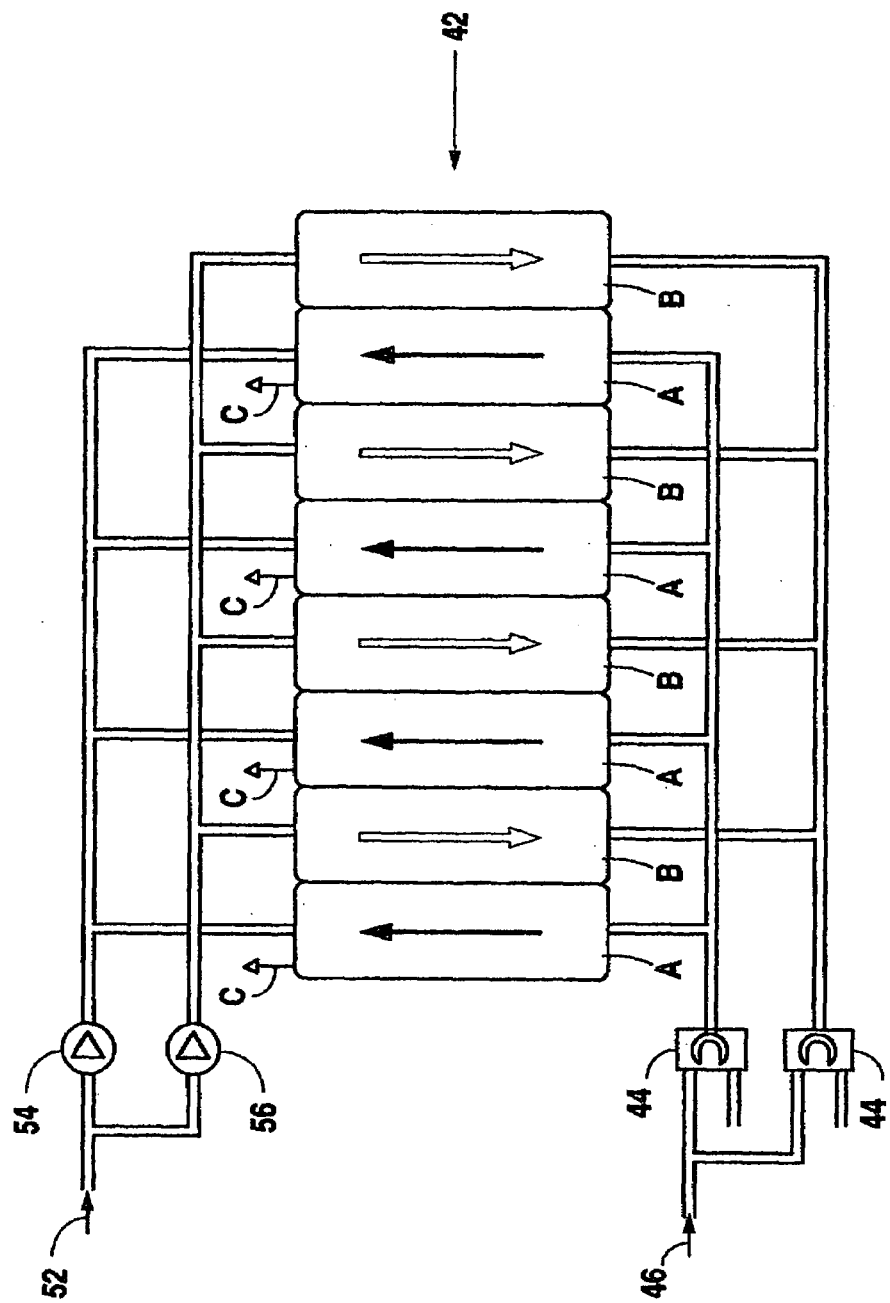
FIG. 2 is a schematic diagram of a patient support mattress having an air flow control system.

FIG. 2 illustrates in more detail how air is supplied to the mattress 42, so that alternate cells are pressurized with high and low pressure air in successive cycles. As shown, there are two interleaved sets of cells or compartments A and B, both of which are connected continuously to a source of cold air at low pressure by means of valves 54 and 56 respectively. In the general arrangement of FIG. 1a, these will normally be connected via line 52 to the tent inlet duct 4 which supplies the air tent 2, and will therefore provide little supporting effect for the patient (being at low pressure) but will have fairly substantial cooling capacity.

The high pressure air supply through conduit 46 driven by the blower 48 (as described above with reference to FIG. 1a) is connected to each set of cells A or B, by a respective servo valve 44, and these are activated alternately so that during a first cycle, all cells A are inflated to a high pressure so as to support the patient while cells B are connected to the tent outlet duct 6 for re-circulation. A controlled amount of leakage is of course permitted through the fabric of each cell, as indicated by arrow C, since the high pressure air cannot escape via the non-return valves 54, 56 (as shown in FIG. 1a and FIG. 2). Since the high pressure air supply via conduit 46 has been subjected to greater pressurization, it is, of course, at a somewhat higher temperature than the low pressure supply, and thus, primarily performs a supporting function rather than a cooling function for the patient's body.

At the same time, however, the cells B are receiving the supply of colder air via line 52 at relatively low pressure, so these cells primarily provide a cooling function rather than a supporting function.

At the next cycle, the high pressure air supply is shut off from the cells A, by operating their respective servo valve 44 and instead, they are connected to the tent outlet duct 6 for re-circulation so that they now act primarily to provide cooling, as passageways for the cold air supply via line 52. At the same time, the cells B are connected to the high pressure supply, so as to take over the patient supporting function, in the same way, as described above for the cells A in the previous cycle.

In this way, each region of the patient's body is alternately supported by the high pressure, or subjected to cooling, rather than being continuously subjected to high pressure.

FIGS. 3a–3d illustrate one embodiment of an air tent 2. As shown, the air tent comprises a generally semi-cylindrical fabric structure, having a base portion (not visible in the Figure) that is supported on a mattress cover 62 enclosing a mattress structure of the kind described above with reference to FIG. 2. Although the semi-cylindrical shape is beneficial and advantageous, other tent shapes are also suitable and should be understood to fall within the scope of the claims, unless otherwise specified.

As can be seen from the plan view of FIG. 3b, the upper or covering portion of the enclosure comprises a pair of elongate flaps 64 whose adjoining edges can be connected with a Velcro® type seal (i.e., separable complementary hook and loop fasteners) or similar seal 66, each flap being formed with a flexible, transparent inspection panel 68. A head end panel 70 (FIG. 3c) is formed with an aperture 72 for the neck of the patient, to allow the patient's head to protrude from the enclosure, and this aperture 72 is connected to the circular edge of the head end panel 70, by means of a slit 74 to facilitate the process of positioning the patient's neck. This slit is also provided with a Velcro type or similar seal 66 along its adjacent edges, for subsequent closure.

The air tent 2 is also provided with a series of specially adapted apertures 76, for the entry of various conduits and connectors, as will be described in more detail below, while the foot end 60 (FIG. 3d) is provided with a pair of air input ports 61 for air input ducts, as well as a re-circulation aperture 80 for connection to re-circulation and pressure relief valves.

FIGS. 4a, 4b, and 4c illustrate a "full enclosure" version of the air tent 2 of FIGS. 3a, 3b, 3c, and 3d, in which, as depicted in FIGS. 4a and 4b, the enclosure is longer so as to enclose the patient's head. This version includes additional transparent inspection panels 68 in the head region to allow the patient external vision. In this case, of course, the head end panel 70 does not include a neck aperture.

In the embodiments depicted in FIGS. 3a–3d and 4a–c, the air tent 2 is supported by its internal air pressure, which is maintained by air supplied through the tent inlet duct 4. In alternative embodiments described further below, poles, rods, beams, inflatable air tubes, or equivalent support structures are used to support the air tent 2.

FIGS. 5a and 5b illustrate the arrangement by which pipes and conduits are passed through the walls of the air tent 2, with minimum air leakage. Each conduit aperture 76 is provided with a radially collapsible tubular sleeve 78 made of flexible material such as fabric. The tubular sleeve 78 is stitched into the head end panel 70 in the arrangement shown in FIG. 5a and projects from the wall as shown in FIG. 5b. The outer edge of the tubular sleeve 78 is reinforced with a split aluminum anchor ring 92 (FIG. 5c) having a covering of Velcro type material 94 stitched around it. Thus the Velcro-covered ring shown in FIG. 5b forms a reinforced sleeve rim 82 at the outer end of the tube to maintain the tubular sleeve 78 in a generally circular configuration as it is closed around the conduit. This reinforced sleeve rim 82, as well as the tubular sleeve 78 itself, is formed with corresponding splits 84 which enable the tubular sleeve to be closed around a conduit, as explained in more detail below.

Continuing in FIG. 5a, four Velcro type "loop" pads 86 stitched to the head end panel 70 of the air tent 2 surround the tubular sleeve 78. The panel itself includes a slit 88 that extends from the spilt 84 of the tubular sleeve 78 to the outer edge 90 of the panel. In this way, a pipe or conduit (which may for example already be connected to the patient) can be passed into the enclosure, so as to exit through the sleeve 78, without disconnecting either end.

After the conduit has been properly positioned, the reinforced sleeve rim 82 is twisted around and squeezed into engagement with the conduit (not shown in the Figure), and pressed against the Velcro type pads 86. The rim 82 is then attached to the pads, locating the conduit tightly in position. It will be appreciated that this closure system works equally well for a wide range of conduit sizes. In addition, if any particular aperture 76 is not needed, the sleeve 78 can be twisted up more tightly to close the aperture completely (as indicated schematically in FIGS. 3a, 3b, 3c, 3d and FIGS. 4a, 4b, and 4c).

It will be appreciated that the slit 88 (shown in FIG. 5a) is also provided with suitable Velcro type or similar closure means along its adjacent edges, so that the entire closure can be made substantially leak proof, thus reducing significantly the overall re-circulation losses in the system.

Figure 6:
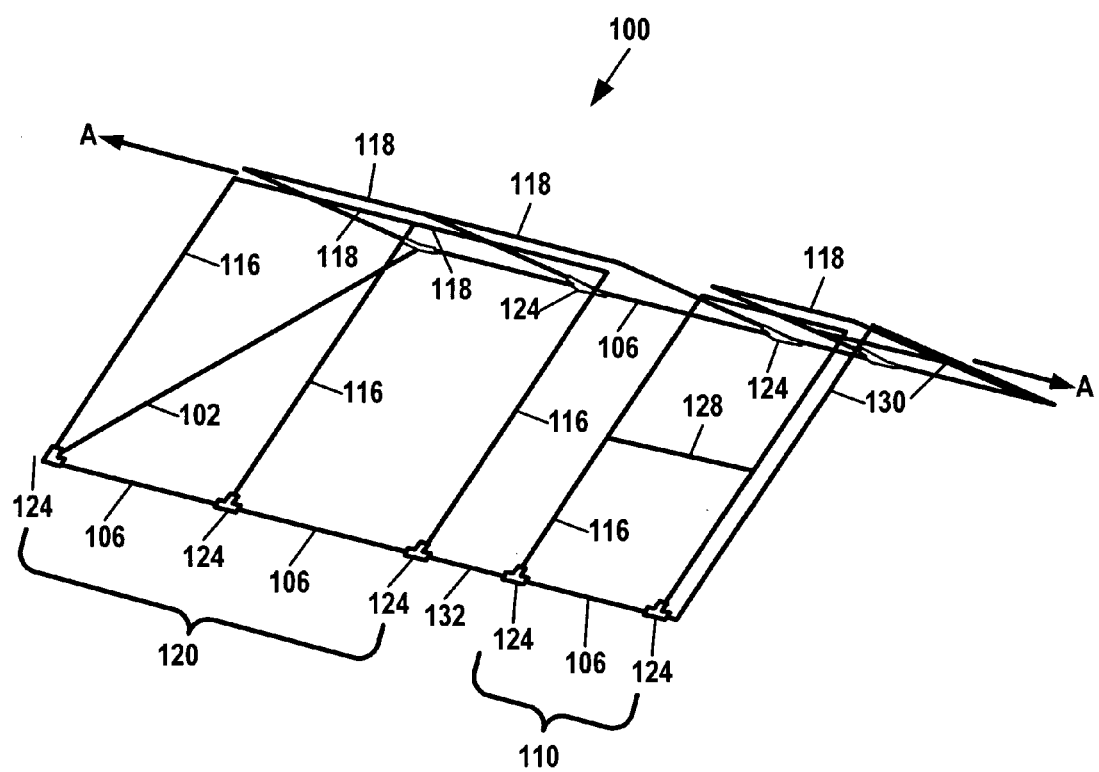
FIG. 6 is a perspective view of one embodiment of a patient enclosure support framework of trusses or rods.

As noted above, in some embodiments, the air tent 2 is supported by its internal air pressure. In an alternative embodiments, however, the air tent 2 is supported by a framework. FIG. 6 depicts a triangle-shaped embodiment of a support framework 100 for an air tent 2, although it will be understood that frameworks with more spacious dimensions may be preferable. The support framework 100 comprises a plurality of poles, rods, braces, or equivalent structural support members to raise and maintain the elongate flaps 64 of the covering portion of the tent 2 above the patient. More particularly, the framework 100 comprises several base members 106, link members 132, rafter members 116, ridge members 118, purlin members 128, and a cross member 102.

Preferably, the framework 100 is at least partially, if not entirely, split along its longitudinal dimension A—A, and the rafter members 116 connected to the base members 106 through pivot joints 124 (or, in the alternative, through separable joints). In this manner, one or more of the split portions of the framework 100 may be pivoted away (or, if separable joints are used, removed altogether) to provide access to the patient. In yet further embodiments, the framework 100 is also split along its transverse dimension into two or more sections to facilitate articulation of the air tent 100 on an articulating bed frame. FIG. 6 shows a division in the framework 100 between an upper body section 110, a lower body section 120, and a head opening frame section 130. In this manner, the upper body section 110 and lower body section 120 can be positioned at angles with respect to each other that correspond with the articulating sections of an articulating bed frame.

Figures 7, 8:
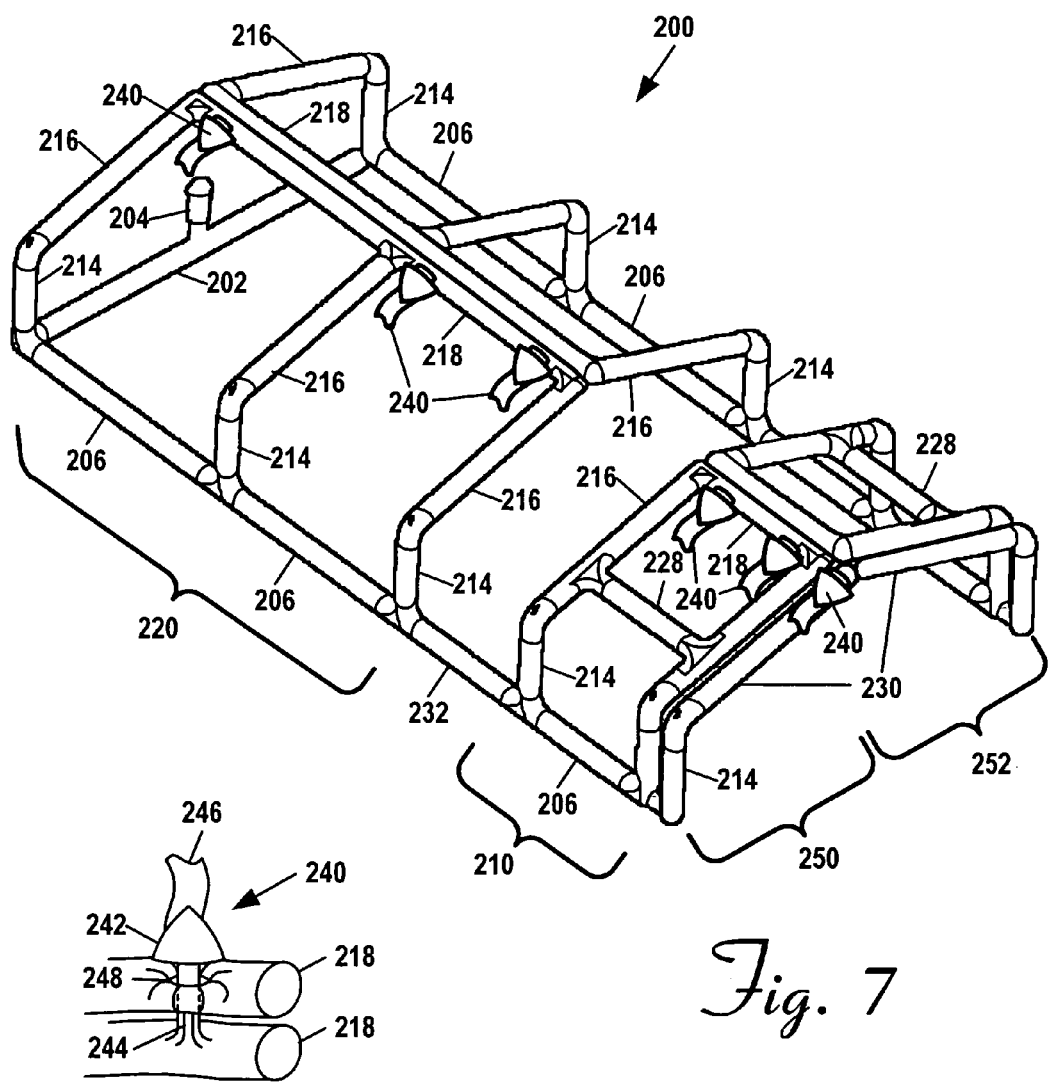
FIG. 7 is a perspective view of one embodiment of a patient enclosure support framework of inflatable tubes.
FIG. 8 is a three-dimensional view of an inflatable connection means for removably connecting parts of the framework together.

FIG. 7 depicts another embodiment of a tubular support framework 200 for an air tent 2. This tubular support framework 200 comprises a plurality of inflatable tubes to support the elongate flaps 64 of the covering portion of the tent 2 above the patient. More particularly, the framework 200 comprises several pneumatically connected feeder tubes 206, link tubes 232, vertical support tubes 214, rafter tubes 216, ridge tubes 218, purlin tubes 228, and a cross tube 202. Preferably, the tubular support framework 200 is provided with a high-pressure inflation source. The tubular support framework 200 may be supplied with air by connection of the air inlet port 204 with the air supply conduit 46, mediated through an independent servo valve or through the bank of servo valves 44 that supply air to the individual cells of the patient supporting mattress 42.

Preferably, the framework 200 is at least partially, if not entirely, split along its longitudinal dimension, between left and right halves 250 and 252, so that one or more of the split portions of the framework 200 may be pivoted away to provide access to the patient. In yet further embodiments, the framework 200 is also split along its transverse dimension into two or more sections to facilitate selective access to the patient and articulation of the air tent 200 on an articulating bed frame. In FIG. 7, the framework 200 is divided between an upper body section 210, a lower body section 220, and a head opening frame section 230. Either half of the upper body section 210 can be pivoted away from the patient to provide access to the upper body of the patient. Likewise, either half of the lower body section 220 can be pivoted away from the patient to provide access to the lower body of the patient.

FIG. 8 is a three-dimensional view of an inflatable quick-connect and quick-release closure means for releasably connecting parts of the framework 200, such as the ridge tubes 218 of the left and right halves of the framework 200, together. An inflatable tube connector 240 protrudes out of a ridge tube 218 on the left or right side 250 or 252 of the framework 200. The ridge tube 218 on the opposite side of the framework 200 has a hole 248 for receiving the inflatable tube connector 240. The tube connector 240 comprises a stem 244, a protuberance 242, and a pull tab 246 for pulling the connector 240 through hole 248. When inflated, the protuberance expands so that the diameter of its outer dimension exceeds the diameter of the hole 248, thereby resisting disconnection. As shown in FIG. 7, several connectors 240 are provided to close the left and right sides 250 and 252 of the framework 200.

The connector 240 can easily be pulled out of corresponding hole 248 by pulling it out. Removal is even easier if the framework (which includes the connectors themselves) is first deflated. The stem 244 and protuberance 242 of the connector 240 are preferably inflatable, but in alternative embodiments may be filled with foam, cushioning material, or other compressible substances.

In operation, the air tent 2 is inflated by supplying high-pressure air to the tubular support framework 200. To gain access to the patient, it is contemplated that a caregiver will operate a user interface (such as a switch or computer input command) to turn off the air supply or a valve to deflate the framework 200. Upon deflation, the framework 200 becomes flexible and can easily be folded into an open position and out of the way. Alternatively, the caregiver may leave the tubular support framework inflated. Because the tubes are preferably constructed of flexible fabric or plastic material, they can easily be folded down while inflated.

Figure 9:
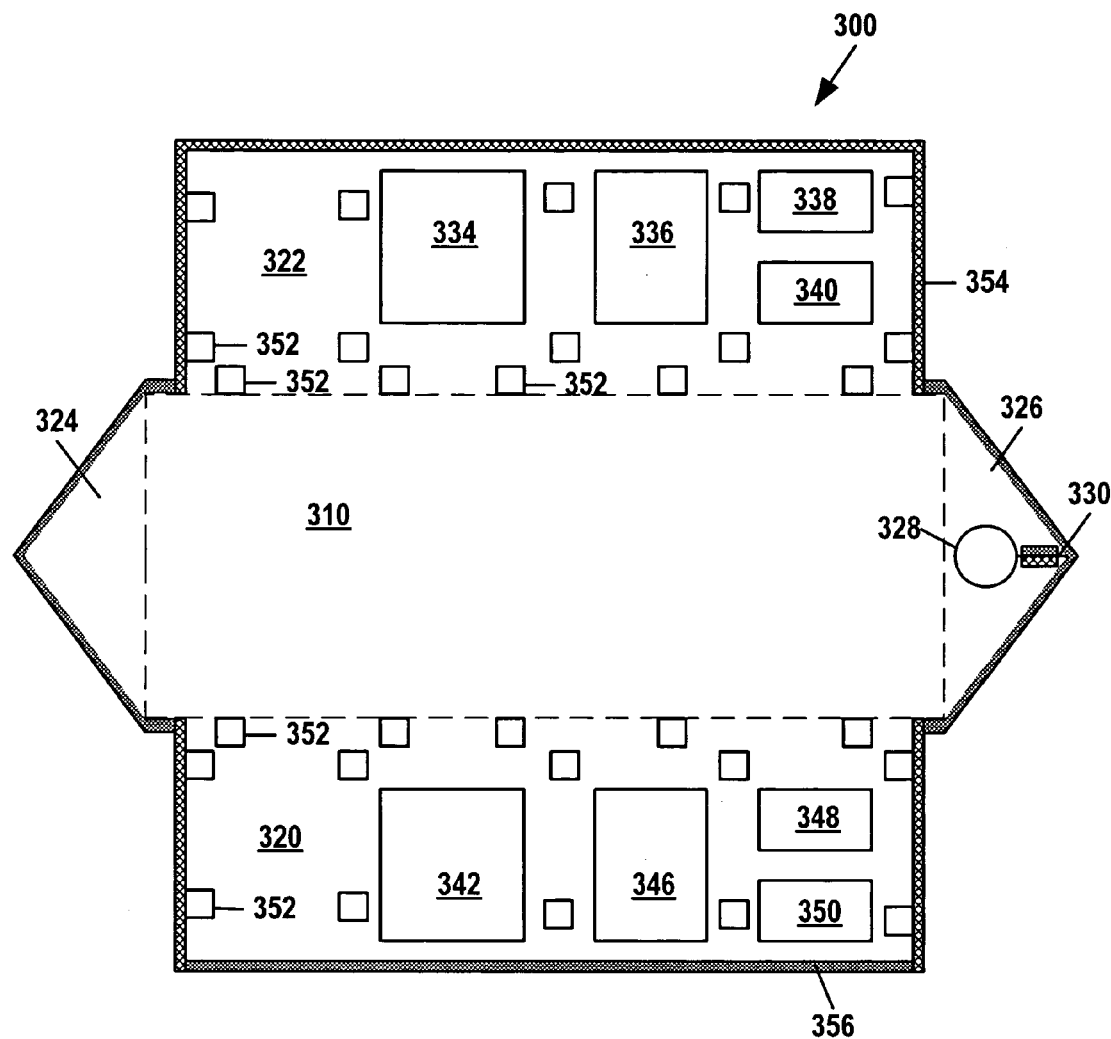
FIG. 9 depicts a layout of one embodiment of a tent designed to cover the patient enclosure framework of FIG. 7.

FIG. 9 depicts a layout of one embodiment of a tent 300 designed to cover the patient enclosure framework of FIG. 7. Tent 300 comprises a bottom sheet 310, a left side 320, a right side 322, a foot drape 325, and a head drape 326. The head drape 310 provides an opening 328 for a patient's head. The head drape 310 also provides a slit 330 that facilitates adjustment of the size of the head opening 328 and placement and removal of the patient and care lines to the patient. Other slits and flaps (not shown) may also be provided in the left side 320, right side 322, and foot drape 324 to facilitate insertion or removal of patient care lines, air supply hoses, and the like.

Clear plastic translucent windows 334, 336, 338, 340, 342, 346, 348, and 350 enable caregivers to see the patient and the patient to see his or her caregivers. A plurality of tube attachment connectors 332 are provided to attach the tent 300 to the tubular support framework 200. Although not shown in FIG. 7, tent 300 may be equipped with many of the same features shown in connection with FIGS. 3a–5c, including but not limited to air input ports 61, conduit apertures 76, and a recirculation aperture 80.

In one embodiment, the tent is also provided with a plurality of Velcro-type loop fasteners 354 and Velcro-type hook fasteners 356 to facilitate a better air seal. In an alternative embodiment, a sufficient number of quick-release connectors 240 are used and a sufficient volume of cool air is pumped into the tent to eliminate the need for Velcro-type fasteners.

Figure 10:
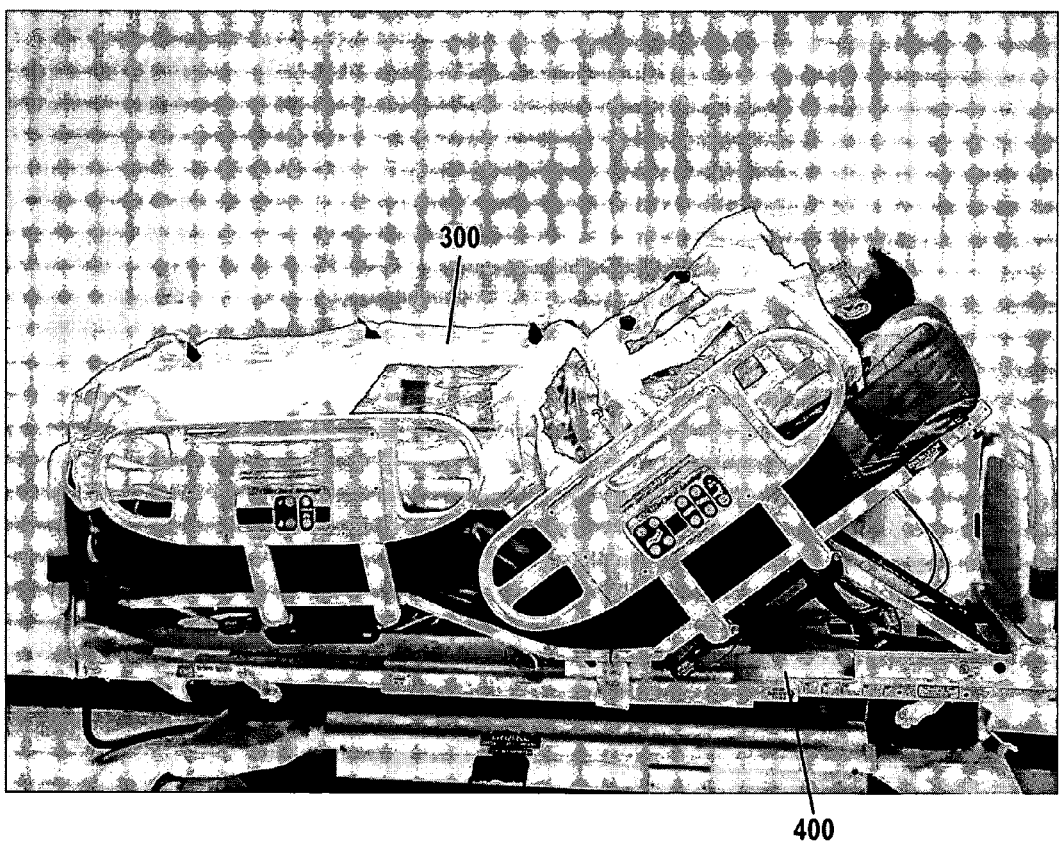
FIG. 10 is a perspective view of an embodiment of a patient support enclosure mounted on an articulating hospital bed frame.
Figure 11:
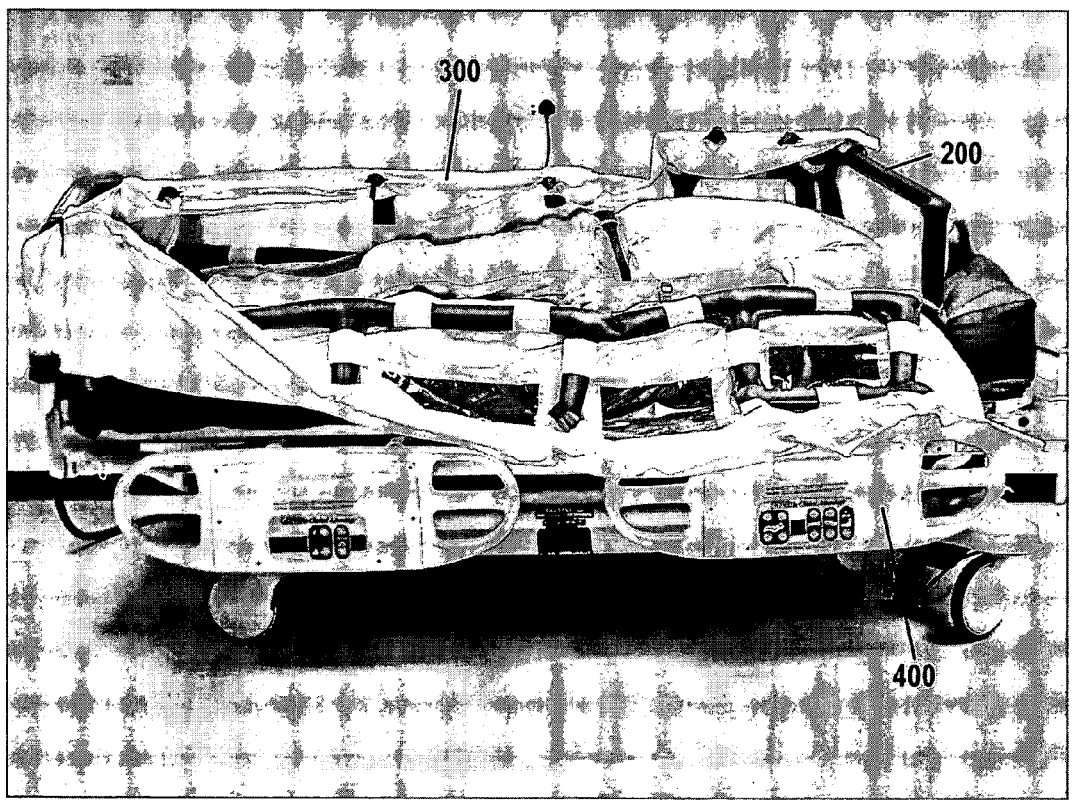
FIG. 11 is a side view of the patient support enclosure of FIG. 10 with one side folded down.
Figure 12:
FIG. 12 is a head-end view of the patient support enclosure of FIG. 10 with one side folded down.

FIGS. 10 through 12 show an embodiment of a patient cooling enclosure comprising the air tent 300 of FIG. 9 with the tubular support framework 200 mounted on an articulating bed frame 400. FIG. 10 shows the air tent 300 in a closed position mounted on a frame in an articulated position. FIGS. 11 and 12 show the air tent 300 in an open position, with the left longitudinal half 250 of the still-inflated framework 200 folded away from the patient to provide access to the patient.

Although the foregoing specific details describe various embodiments of the invention, persons reasonably skilled in the art will recognize that various changes may be made in the details of the apparatus of this invention without departing from the spirit and scope of the invention as defined in the appended claims. Therefore, it should be understood that, unless otherwise specified, this invention is not to be limited to the specific details shown and described herein.

We claim:

1. An apparatus comprising:
   a plurality of sets of interleaved air bags collectively forming a patient supporting surface, each set of interleaved air bags being independently inflatable; and
   a high air pressure source in fluid communication with the air bags; wherein the high air pressure source is operable to alternately inflate the sets of interleaved air bags to periodically relieve alternate regions of the patient's body from pressure;
   a framework of inflatable tubes;
   a patient-enclosing air tent mounted on the framework of inflatable tubes, the inflatable tubes being operable, when inflated, to support the air tent above the patient, wherein the patient enclosing air tent is sized to enclose at least a portion of a single patient except a head portion of the patient;
   an air inlet connected to an air-cooling system for introducing cooled air into the patient enclosing air tent; and
   an outlet connected to the air-cooling system for re-circulating air from the air tent back to the air-cooling system to conserve energy.

2. The apparatus of claim 1, further comprising a coaxial hose having an inner passage to send air into the air tent and an outer coaxial passage to carry air from the air tent.

3. The apparatus of claim 1, further comprising a fluid connection between the air bags and the air cooling system, wherein the air bags are operable to be pressurized with either relatively high flow cold air which assists in cooling the patient but provides relatively little support or with relatively high pressure air which is sufficient to support the patient but which provides relatively less cooling effect.

4. An apparatus comprising:
   a plurality of air bags collectively forming a patient supporting surface;
   a high air pressure source in fluid communication with the air bags; and
   a fluid connection between the air bags and an air cooling system, wherein the air bags can be pressurized with either relatively high flow cold air which assists in cooling the patient but provides relatively little support or with relatively high pressure air which is sufficient to support the patient but which provides relatively less cooling effect;
   a framework of inflatable tubes;
   a patient-enclosing air tent mounted on the framework of inflatable tubes, the inflatable tubes being operable, when inflated, to support the air tent above the patient, wherein the patient enclosing air tent is sized to enclose at least a portion of a single patient except a head portion of the patient;

an air inlet connected to the air-cooling system for introducing cooled air into the patient enclosing air tent; and an outlet connected to the air-cooling system for re-circulating air from the air tent back to the air-cooling system to conserve energy.

5. The apparatus of claim 4, further comprising at least one aperture on the air tent for removable conduits, the aperture comprising a sleeve of flexible material operable to be tightened around a conduit by twisting the sleeve so that it collapses radially about the conduit.

6. The apparatus of claim 5, wherein when no conduit is present the sleeve is operable to be twisted tightly enough to close the aperture completely.

7. The apparatus of claim 5, wherein the framework of inflatable tubes are operable to be moved between a closed position extending over the patient and an open position extending away from the patient, the framework including one or more inflatable connectors to releasably secure the framework in the closed position.

8. The apparatus of claim 7, wherein the framework of inflatable tubes has a longitudinal dimension, wherein the framework of inflatable tubes is split along the longitudinal dimension between left and right halves, where each half can be moved from the closed position to the open position.

9. The apparatus of claim 7, wherein at least one aperture is provided in the framework of inflatable tubes for receiving the inflatable connector.

10. The apparatus of claim 7, wherein the inflatable connector comprises a stem and an inflatable protuberance having an outer dimension that, when the inflatable protuberance is inflated, exceeds the diameter of the aperture.

11. The apparatus of claim 10, wherein the inflatable connector further comprises a tab attached to the protuberance to facilitate insertion of the protuberance through the aperture.

12. An apparatus comprising:
a pressurized air source;
a framework of inflatable tubes in fluid connection with the pressurized air source, the framework of inflatable tubes being split between left and right halves along a longitudinal dimension of the framework, each half further comprising an upper body section and a lower body section; each section of each half being independently operable to be moved between a closed position extending over the patient and an open position extending away from the patient;
a patient-enclosing air tent mounted on the framework of inflatable tubes, the inflatable tubes being operable, when inflated, to support the air tent above the patient;
an air-cooling system to provide cold air to the interior of the patient-enclosing air tent, the cold air to affect a core temperature of the patient; and
an outlet connected to the air-cooling system for re-circulating air from the air tent back to the air-cooling system to conserve energy.

13. The apparatus of claim 12, the patient-enclosing air tent having a plurality of transparent windows to enable visual contact between the patient and another person exterior of the patient-enclosing air tent.

14. The apparatus of claim 12, the framework including:
at least one inflatable connector to releasably secure the left and right halves of the upper body section together; and
at least one additional inflatable connector to releasably secure the left and right halves of the lower body section together.

15. The apparatus of claim 14, the framework further including:
at least one corresponding aperture in the upper body section of the framework for receiving the at least one inflatable connector; and
at least one additional corresponding aperture in the lower body section of the framework for receiving the at least one additional inflatable connector.

16. The apparatus of claim 15, wherein the inflatable connectors each comprise a stem and an inflatable protuberance having an outer dimension that, when the inflatable protuberance is inflated, exceeds the diameter of the corresponding aperture.

17. The apparatus of claim 16, wherein the inflatable connector further comprises a tab attached to the protuberance to facilitate insertion of the protuberance through the corresponding aperture.

18. An apparatus comprising:
a plurality of air bags collectively forming a patient supporting surface;
a high-pressure air source in fluid connection with the air bags, the high-pressure air source operable to provide sufficient air pressure to support the patient;
a framework of inflatable tubes also in fluid connection with the high-pressure air source;
a patient-enclosing air tent mounted on the framework of inflatable tubes, the inflatable tubes being operable, when inflated, to support the air tent above the patient; and
an air-cooling system to provide cold air to the interior of the patient-enclosing air tent, the cold air to affect a core temperature of the patient.

19. The apparatus of claim 18, wherein at least one aperture is provided in the framework of inflatable tubes for receiving an inflatable connector.

20. The apparatus of claim 18, including an outlet connected to the air-cooling system for re-circulating air from the air tent back to the air-cooling system to conserve energy.

* * * * *